United States Patent
Onishi et al.

(10) Patent No.: US 8,673,937 B2
(45) Date of Patent: Mar. 18, 2014

(54) EYE-DROP PREPARATION AND USE THEREOF

(75) Inventors: Yoshinao Onishi, Osaka (JP); Shinichi Ishikawa, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 141 days.

(21) Appl. No.: 12/988,895

(22) PCT Filed: Apr. 23, 2009

(86) PCT No.: PCT/JP2009/058042
§ 371 (c)(1),
(2), (4) Date: Jan. 10, 2011

(87) PCT Pub. No.: WO2009/131164
PCT Pub. Date: Oct. 29, 2009

(65) Prior Publication Data
US 2011/0105558 A1    May 5, 2011

(30) Foreign Application Priority Data
Apr. 23, 2008  (JP) ................................ 2008-112069

(51) Int. Cl.
*A61K 31/47* (2006.01)
*A61K 31/215* (2006.01)

(52) U.S. Cl.
USPC ............................. 514/312; 514/530; 514/912

(58) Field of Classification Search
USPC ......................................... 514/312, 530, 912
See application file for complete search history.

(56) References Cited

U.S. PATENT DOCUMENTS 6,399,605 B1    6/2002  Maurin et al.

FOREIGN PATENT DOCUMENTS

| EP | 1321144 A1 | 6/2003 |
|---|---|---|
| JP | 2001-81048 | 3/2001 |
| JP | 2002-511430 | 4/2002 |
| JP | 2002-161037 | 6/2002 |
| JP | 2004-182719 | 7/2004 |
| JP | 2007-63265 | 3/2007 |

OTHER PUBLICATIONS

Kawai, H. et al., "Ocular Hypotensive Effect of Combined Instillation;" "Carteolol to Latanoprost no Heiyo ni yoru Gan'atsu Koka Koka," Dai 56 Kai Nippon Rinsho Ganka Gakkai Koenshu 4, vol. 57, No. 5, pp. 709-713, (May 15, 2003).
Haneda, M. et al., "Comparison of the Additive Effects of Nipradilol and Carteolol to Latanoprost in Open-Angle Glaucoma," Jpn. J. Ophthalmol, vol. 50, No. 1, pp. 33-37, (2006).
International Search Report from the Japanese Patent Office for International Application No. PCT/JP2009/058042, mailed Jun. 9, 2009.
The Index Merck, 1996, Merck & Co., Inc., USA, XP002689732, item 1917, pp. 306-307.
Prodrugs: challenges and rewards, part 1, 2007, Springer, USA XP002689733, col. 127, lines 5-8.
Extenoed European Search Report for EP Application No. 09735992.1 dated Jun. 27, 2013.
Chinese Office Action dated Aug. 25, 2011.

*Primary Examiner* — Zohreh Fay
(74) *Attorney, Agent, or Firm* — Finnegan, Henderson, Farabow, Garrett & Dunner, L.L.P.

(57) ABSTRACT

Disclosed is a technique for preventing the decomposition of latanoprost (a thermally unstable substance) contained in an eye-drop solution to stabilize the eye-drop solution. Specifically disclosed is an eye-drop preparation comprising latanoprost and carteolol hydrochloride. By adding carteolol hydrochloride to an eye-drop solution containing latanoprost which is a thermally unstable substance and is likely to be adhered on the surface of a container, it becomes possible to prevent the decomposition of latanoprost in the eye-drop solution and also prevent the loss of latanoprost caused by the adsorption of latanoprost on the surface of a container.

5 Claims, No Drawings

EYE-DROP PREPARATION AND USE THEREOF

TECHNICAL FIELD

The present invention relates to an eye-drop preparation and use thereof.

BACKGROUND ART

Latanoprost has a chemical name of isopropyl-(Z)-7-[(1R, 2R,3R,5S)3,5-dihydroxy-2-[(3R)-3-hydroxy-5-phenylpentyl]cyclopentyl]-5-heptenoate and is used as a prostaglandin analog for the treatment of glaucoma. The administration route of latanoprost is ocular instillation and an ophthalmic solution containing 0.005% of latanoprost is commercially available. However, latanoprost itself is a thermally unstable drug and tends to decompose in an ophthalmic solution when temperature becomes higher than normal temperature (25° C.). For this reason, a latanoprost-containing ophthalmic solution has to be stored in a cold place (2 to 8° C.) under light shielding. NON-PATENT LITERATURE 1 is an article which reports the stability of a latanoprost-containing ophthalmic solution to temperature and light.

As for a latanoprost-containing ophthalmic solution, its storage temperature may increase during distribution or storage in some cases and decomposition of a part of latanoprost is therefore unavoidable. As far as a latanoprost-containing ophthalmic solution is stored in a cold place, the decomposition of thermally unstable latanoprost can be controlled. Since such an ophthalmic solution is exposed to various environments, however, the development of technology which prevents the decomposition of latanoprost by a method other than cold storage is desired.

PRIOR ART DOCUMENT

Non-Patent Literature

NON-PATENT LITERATURE 1: Journal of Glaucoma, 10(5), 401-405, 2001

DISCLOSURE OF THE INVENTION

Problem to be Solved by the Invention

An object of the present invention is to provide technology which prevents the decomposition of thermally unstable latanoprost contained in an ophthalmic solution and stabilize the ophthalmic solution.

Technical Solutions

The present inventors had been repeated earnest investigations to solve the above-mentioned problem. As a result, it was found that when carteolol hydrochloride was added to an ophthalmic solution containing thermally unstable latanoprost, surprisingly, the adsorption of latanoprost during preparing the ophthalmic solution and the decomposition of latanoprost in the ophthalmic solution were effectively controlled to greatly improve the stability of the ophthalmic solution. The present invention has been completed based on such findings.

The present invention provides an eye-drop preparation and a method for the use thereof shown in the following items 1 to 7.

Item 1. An eye-drop preparation containing latanoprost and carteolol hydrochloride.

Item 2. The eye-drop preparation according to Item 1, further containing alginic acid.

Item 3. The eye-drop preparation according to Item 1 or 2, wherein the latanoprost is present at 0.0001 to 0.1% (w/v).

Item 4. The eye-drop preparation according to Item 1 or 2, wherein the carteolol hydrochloride is present at 0.1 to 5% (w/v).

Item 5. The eye-drop preparation according to Item 2, wherein the alginic acid is present at 0.1 to 5% (w/v).

Item 6. A method for controlling decomposition of latanoprost in an ophthalmic solution containing thermally unstable latanoprost by adding carteolol hydrochloride to the ophthalmic solution.

Item 7. A method for controlling loss of latanoprost due to adhesion to a container by adding carteolol hydrochloride to an ophthalmic solution containing latanoprost easily adsorbing to a container.

The eye-drop preparation of the present invention contains latanoprost and carteolol hydrochloride as active ingredients.

Carteolol hydrochloride which is used in the present invention has a chemical name of 5-[(2RS)-3-(1,1-dimethylethyl) amino-2-hydroxypropyloxy]-3,4-dihydroquinolin-2(1H)-one monohydrochloride and is a compound used as a beta-blocker for the treatment of glaucoma.

The concentration of latanoprost in the eye-drop preparation of the present invention is not particularly limited as far as latanoprost produces a desired drug action. However, the concentration of latanoprost is preferably 0.0001 to 0.1% (W/V), and more preferably 0.001 to 0.02% (W/V).

The concentration of carteolol in the eye-drop preparation of the present invention is not particularly limited. However, the concentration of carteolol is preferably 0.1 to 5% (W/V), more preferably 0.5 to 3% (W/V), and still more preferably 1 to 2% (W/V).

The eye-drop preparation of the present invention can be easily prepared by a widely-used method. Known ingredients such as a tonicity agent, a buffer, a pH adjusting agent, an antiseptic agent, a solubilizer and a thickener, etc. can be added as appropriate to the eye-drop preparation of the present invention.

The tonicity agent can include, for example, glycerol, propylene glycol, polyethylene glycol, trehalose, maltose, sucrose, glucose, sorbitol, mannitol, sodium chloride, potassium chloride, calcium chloride and magnesium chloride, etc.

The buffer can include, for example, phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc.

The pH adjusting agent can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc.

The antiseptic agent can include, for example, benzalkonium chloride, benzododecinium bromide, chlorhexidine gluconate, benzethonium chloride, sorbic acid, potassium sorbate, methyl parahydroxybenzoate, ethyl parahydroxybenzoate and butyl parahydroxybenzoate, etc.

The solubilizer can include, for example, vegetable oils and fats or the like such as polysorbate 80, polyoxyethylene hydrogenated castor oil 60, macrogol 4000, polyvinyl alcohol, tyloxapol, polyoxyethylene polyoxypropylene glycol and soybean oil, etc.

The concentration of the solubilizer is not particularly limited. However, the concentration is preferably 0.1 to 5% (W/V), more preferably 0.5 to 3% (W/V) and still more preferably 1 to 2% (W/V).

The thickener can include, for example, hydroxypropyl methyl cellulose, hydroxypropyl cellulose, polyvinyl alcohol, carboxyvinyl polymer, polyvinylpyrrolidone, carboxymethyl cellulose, polyacrylic acid, sodium polyacrylate, alginic acid and sodium alginate, etc. Particularly, the prolongation of actions and effects can be expected by adding alginic acid or sodium polyacrylate to the eye-drop preparation of the present invention. When alginic acid is used, pH is preferably adjusted to 6 to 8 by an alkali base. The concentration of the thicker is not particularly limited. However, the concentration is preferably 0.1 to 5% (W/V), more preferably 0.5 to 2% (W/V).

The pH of the eye-drop preparation of the present invention is preferably about 3 to 9, particularly preferably about 4 to 8 and more preferably 6 to 8.

Advantageous Effects of Invention

The eye-drop preparation of the present invention has the following advantages:
(1) Addition of carteolol hydrochloride to an eye-drop preparation can effectively control the decomposition of latanoprost in the eye-drop preparation and thereby greatly improve the stability of the eye-drop preparation. For this reason, troublesome effort to store the eye-drop preparation of the present invention in a cold place can be saved.
(2) Addition of latanoprost and carteolol hydrochloride to a single eye-drop preparation causes no harmful effects. For this reason, sufficient intervals between administrations required upon administration of two or more eye-drop preparations in combination are not required. Also, the reduction in the number of ocular instillations per day can enhance the convenience of users. Furthermore, the improvement of eye-drop compliance can improve the control of intraocular pressure.
(3) Addition of latanoprost and carteolol hydrochloride to a single eye-drop preparation intensifies the effect of lowering intraocular pressure.
(4) Since latanoprost and carteolol hydrochloride are contained in a single eye-drop preparation, the amount of exposure to antiseptic agents can be decreased compared with a case where two or more eye-drop preparations are used in combination. As a result, a risk for development onset of adverse drug reactions such as corneal disorder can be decreased.

DESCRIPTION OF EMBODIMENTS

The present invention will be further clarified with reference to the following examples.

Preparation Example 1

2 g of carteolol hydrochloride, 5.2 mg of latanoprost, 0.04 g of sodium dihydrogen phosphate dihydrate, 0.1 g of disodium hydrogen phosphate dodecahydrate and 0.54 g of sodium chloride were weighed and about 80 ml of purified water was added thereto. The mixture was stirred while heating to about 60° C. to allow dissolution. After returning it to room temperature, the resultant solution was made exactly 100 ml by adding purified water thereto to prepare an eye-drop preparation of pH 6.8.

Preparation Example 2

An eye-drop preparation of pH 6.8 was prepared in a manner similar to that in Preparation Example 1 except that 5 mg of benzalkonium chloride was added to the composition of Preparation Example 1.

Preparation Example 3

An eye-drop preparation of pH 6.8 was prepared in a manner similar to that in Preparation Example 1 except that 20 mg of benzalkonium chloride was added to the composition of Preparation Example 1.

Preparation Example 4

1 g of carteolol hydrochloride, 5.2 mg of latanoprost, 0.04 g of sodium dihydrogen phosphate dihydrate, 0.1 g of disodium hydrogen phosphate dodecahydrate were dissolved in about 80 ml of purified water. Further, 1 g of alginic acid, 0.44 g of sodium chloride, and appropriate amounts of a sodium hydroxide solution and purified water were added thereto to prepare 100 ml of an eye-drop preparation of pH 6.5.

Preparation Example 5

2 g of carteolol hydrochloride, 5.2 mg of latanoprost, 0.04 g of sodium dihydrogen phosphate dihydrate, 0.1 g of disodium hydrogen phosphate dodecahydrate were dissolved in about 80 ml of purified water. Further, 1 g of alginic acid, 0.44 g of sodium chloride, and appropriate amounts of a sodium hydroxide solution and purified water were added thereto to prepare 100 ml of an eye-drop preparation of pH 6.5.

Preparation Example 6

1 g of carteolol hydrochloride, 5.2 mg of latanoprost, 0.04 g of sodium dihydrogen phosphate dihydrate, 0.1 g of disodium hydrogen phosphate dodecahydrate were dissolved in about 80 ml of purified water. Further, 2 g of alginic acid, 0.3 g of sodium chloride, and appropriate amounts of a sodium hydroxide solution and purified water were added thereto to prepare 100 ml of an eye-drop preparation of pH 6.5.

Preparation Example 7

2 g of carteolol hydrochloride, 5.2 mg of latanoprost, 0.04 g of sodium dihydrogen phosphate dihydrate, 0.1 g of disodium hydrogen phosphate dodecahydrate were dissolved in about 80 ml of purified water. Further, 2 g of alginic acid, 0.3 g of sodium chloride, and appropriate amounts of a sodium hydroxide solution and purified water were added thereto to prepare 100 ml of an eye-drop preparation of pH 6.5.

Preparation Example 8

1 g of carteolol hydrochloride, 5.2 mg of latanoprost, 0.04 g of sodium dihydrogen phosphate dihydrate, 0.1 g of disodium hydrogen phosphate dodecahydrate, and 0.54 g sodium chloride were dissolved in purified water to make exactly 100 ml to prepare an eye-drop preparation of pH 6.8.

Preparation Example 9

1 g of carteolol hydrochloride, 5.2 mg of latanoprost, 1.5 g of boric acid, 0.3 g of sodium chloride and appropriate amounts of a sodium hydroxide solution and purified water were mixed to prepare 100 ml of an eye-drop preparation of pH 6.5.

Preparation Example 10

1 g of carteolol hydrochloride, 5.2 mg of latanoprost, 2 g of boric acid and appropriate amounts of a sodium hydroxide solution and purified water were mixed to prepare 100 ml of an eye-drop preparation of pH 6.5.

Preparation Example 11

2 g of carteolol hydrochloride, 5.2 mg of latanoprost, 1.5 g of boric acid, 0.3 g of sodium chloride and appropriate amounts of a sodium hydroxide solution and purified water were mixed to prepare 100 ml of an eye-drop preparation of pH 6.5.

Preparation Example 12

2 g of carteolol hydrochloride, 5.2 mg of latanoprost, 2 g of boric acid and appropriate amounts of a sodium hydroxide solution and purified water were mixed to prepare 100 ml of an eye-drop preparation of pH 6.5.

Preparation Example 13

2 g of carteolol hydrochloride, 5.2 mg of latanoprost, 1.5 g of boric acid, 1% glycerol and appropriate amounts of a sodium hydroxide solution and purified water were mixed to prepare 100 ml of an eye-drop preparation of pH 6.5.

Preparation Example 14

2 g of carteolol hydrochloride, 5.2 mg of latanoprost, 2 g of boric acid and appropriate amounts of a sodium hydroxide solution and purified water were mixed to prepare 100 ml of an eye-drop preparation of pH 6.5.

Preparation Example 15

2 g of carteolol hydrochloride, 5.2 mg of latanoprost, 1.5 g of boric acid, 1 g of alginic acid and appropriate amounts of a sodium hydroxide solution and purified water were mixed to prepare 100 ml of an eye-drop preparation of pH 6.5.

Preparation Example 16

2 g of carteolol hydrochloride, 5.2 mg of latanoprost, 2 g of boric acid, alginic acid and appropriate amounts of a sodium hydroxide solution and purified water were mixed to prepare 100 ml of an eye-drop preparation of pH 6.5.

Preparation Example 17

1 g of carteolol hydrochloride, 21 mg of latanoprost, 0.1 g of polysorbate 80, 0.04 g of sodium dihydrogen phosphate dihydrate and 0.1 g of disodium hydrogen phosphate dodecahydrate and 0.54 g of sodium chloride were mixed and dissolved by adding purified water thereto to make exactly 100 ml and to prepare an eye-drop preparation of pH 6.8.

Preparation Example 18

1 g of carteolol hydrochloride, 21 mg of latanoprost, 0.1 g of polyoxyethylene hydrogenated castor oil 60, 0.04 g of sodium dihydrogen phosphate dihydrate, 0.1 g of disodium hydrogen phosphate dodecahydrate and 0.54 g of sodium chloride were mixed and dissolved by adding purified water thereto to make exactly 100 ml and to prepare an eye-drop preparation of pH 6.8.

Comparative Preparation Example 1

After measuring 5.2 mg of latanoprost, 0.04 g of sodium dihydrogen phosphate dihydrate, 0.1 g of disodium hydrogen phosphate dodecahydrate and 0.54 g of sodium chloride, about 80 ml of purified water was added thereto. The mixture was stirred while heating to about 60° C. to allow dissolution. After returning to room temperature, the resultant solution was made exactly 100 ml by adding purified water thereto to prepare an eye-drop preparation of pH 6.8.

Comparative Preparation Example 2

An eye-drop preparation of pH 6.8 was prepared in a manner similar to that in Comparative Preparation Example 1 except that 5 mg of benzalkonium chloride was added to the composition of Comparative Preparation Example 1.

Comparative Preparation Example 3

An eye-drop preparation of pH 6.8 was prepared in a manner similar to that in Comparative Preparation Example 1 except that 20 mg of benzalkonium chloride was added to the composition of Comparative Preparation Example 1.

Test for Thermal Stability 4 ml of each of eye-drop preparations obtained by Preparation Examples 1 to 3 and Comparative Preparation Examples 1 to 3 was separately filled in a stoppered glass tube. Each of the tubes was sealed and stored at 70° C. for 1 week. After that, the contents of latanoprost were determined by high performance liquid chromatography (HPLC) to measure the content rate with regard to the amount of latanoprost fed into each of the preparations (at the start and after storage at 70° C. for 1 week). The test result is shown in Table 1.

|  | Content rate with regard to the amount of latanoprost fed into the preparation | |
| --- | --- | --- |
|  | at the start | after storage at 70° C. for 1 week |
| Preparation Example 1 | 96.1 | 91.4 |
| Preparation Example 2 | 95.2 | 90.1 |
| Preparation Example 3 | 94.8 | 90.1 |
| Comparative Preparation Example 1 | 81.7 | 75.0 |
| Comparative Preparation Example 2 | 80.9 | 68.9 |
| Comparative Preparation Example 3 | 82.0 | 72.0 |

As seen in Table 1, the content rates of latanoprost immediately after preparation were higher in the ophthalmic solutions to which carteolol hydrochloride was added (Preparation Examples 1 to 3) then in the ophthalmic solutions to which no carteolol hydrochloride was added (Comparative Preparation Examples 1 to 3), confirming that the loss of latanoprost due to adhesion was smaller for the former.

Further, the residual rates of latanoprost of the solutions after storage at 70° C. for 1 week were calculated from the values of Table 1 (the content rates measured at the start and after storage at 70° C. for 1 week) and it was confirmed that Preparation Examples 1 to 3 had higher residual rates compared with Comparative Preparation Examples 1 to 3.

Furthermore, compared with Comparative Preparation Example 1, Comparative Preparation Examples 2 and 3 had lower residual rates. Accordingly, it was found that addition of benzalkonium chloride increased thermal instability. On the other hand, Preparation Examples 2 and 3 had residual rates almost equivalent to that of Preparation Example 1 in which no benzalkonium chloride was added. Therefore, it was confirmed that carteolol hydrochloride improved the instability due to benzalkonium chloride.

Thus, it was confirmed that addition of carteolol to an ophthalmic solution containing latanoprost which was thermally unstable and had adhesiveness could prevent adhesion to equipment and materials for preparing a drug solution or a container of an eye-drop preparation as well as effectively control the decomposition of thermally unstable latanoprost in an ophthalmic solution to allow stable storage.

The invention claimed is:

1. An eye-drop preparation comprising latanoprost and carteolol hydrochloride.

2. The eye-drop preparation according to claim 1, further comprising alginic acid.

3. The eye-drop preparation according to claim 1 or 2, wherein the latanoprost is present at 0.0001 to 0.1% (w/v).

4. The eye-drop preparation according to claim 1 or 2, wherein the carteolol hydrochloride is present at 0.1 to 5% (w/v).

5. The eye-drop preparation according to claim 2, wherein the alginic acid is present at 0.1 to 5% (w/v).

* * * * *

UNITED STATES PATENT AND TRADEMARK OFFICE
CERTIFICATE OF CORRECTION

| | |
|---|---|
| PATENT NO. | : 8,673,937 B2 |
| APPLICATION NO. | : 12/988895 |
| DATED | : March 18, 2014 |
| INVENTOR(S) | : Onishi et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this
Eleventh Day of August, 2015

Michelle K. Lee
*Director of the United States Patent and Trademark Office*